United States Patent [19]

Valentini et al.

[11] Patent Number: 4,995,385
[45] Date of Patent: Feb. 26, 1991

[54] INHALER WITH REGULAR COMPLETE EMPTYING OF THE CAPSULE

[75] Inventors: Luigi Valentini; Giancarlo Ceschel, both of Milan, Italy

[73] Assignee: Phidea S.P.A., Milan, Italy

[21] Appl. No.: 483,744

[22] Filed: Feb. 23, 1990

[30] Foreign Application Priority Data

Feb. 23, 1989 [IT]  Italy ................... 19539 A/89

[51] Int. Cl.$^5$ ........................................... A61M 15/08
[52] U.S. Cl. ...................... 128/203.21; 128/203.15; 128/203.23
[58] Field of Search ............... 128/203.21, 203.15, 128/203.23

[56] References Cited

U.S. PATENT DOCUMENTS 4,069,819  1/1978  Valentini ................... 128/203.15

Primary Examiner—Edgar S. Burr
Assistant Examiner—Eric P. Raciti
Attorney, Agent, or Firm—Fisher, Christen & Sabol

[57] ABSTRACT

An inhaler (10) for administering medicaments in finely divided form contained in capsules comprises a nebulization chamber (42) and a device (16) for piercing the capsule. That end surface of the nebulization chamber containing the holes (48, 49, 50) for the discharge of air laden with the finely divided medicament is shaped such that the capsule, when resting on it, does not impede air passage through any of the discharge holes. The nebulization chamber, at least in that part thereof closest to said discharge holes, tapers towards that end surface of the chamber comprising the discharge holes.

7 Claims, 2 Drawing Sheets

INHALER WITH REGULAR COMPLETE EMPTYING OF THE CAPSULE

DESCRIPTION

This invention relates to inhalers, i.e. those devices for administering medicaments in finely divided form contained in capsules by inhalation.

In particular, reference should be made to the inhaler described in U.S. Pat. No. 4,069,819, one of the two inventors of which is also one of the two inventors of the present invention. Said patent describes an inhaler of overall cylindrical shape comprising a body enclosing an axially extending nebulization chamber. A capsule containing the medicament in finely divided form is placed in the chamber. The capsules of this type have an overall cylindrical shape with their two ends shaped as a spherical cap. The nebulization chamber is of overall cylindrical shape and has a substantially larger cross-section than the cross-section of the capsule to be placed in the chamber. This latter communicates with the outside through air inlet apertures in the chamber wall at or in proximity to one end of the chamber and shaped to generate a swirling air flow through the chamber during inhalation. The chamber also communicates with the outside through air discharge apertures provided in the other spherical cap-shaped end of the chamber and opening into an axial discharge duct.

The inhaler is also provided with a piercing device for forming two or more holes in one of the spherical cap-shaped ends of the capsule, which has previously been inserted in the nebulization chamber.

When the capsule has been pierced the user brings the inhaler up to his nostril or mouth and breathes in. On breathing in, the particular arrangement of the air inlet holes generates within the nebulization chamber a swirling air flow which moves the pierced capsule so that it undergoes rotation about its axis, rotation along the a chamber walls, and precession of said axis of rotation, in addition to undergoing vibratory movements. These capsule movements cause the medicament in finely divided form to escape through its holes, so that the powder is entrained outwards by said air flow. This latter passes through said discharge apertures and flows along the subsequent discharge duct until it reaches either the oral cavity or the nasal cavity of the patient, as the case may be.

However, the aforesaid inhaler has certain drawbacks. In this respect it has been found that in a large number of cases the emptying of the capsule is irregular and incomplete, with consequent difficulties in administering the finely divided medicament.

The object of the present invention is to obviate said drawbacks by providing an inhaler which always results in regular and complete emptying of the capsule.

The inventor of the present invention has discovered that the irregular and incomplete emptying of the capsule occurs when the movement of the capsule during inhalation randomly degenerates into a rolling movement along the side walls of the cylindrical nebulization chamber. A further situation in which regular complete emptying of the capsule is not obtained occurs when this latter is obstructed in its movements by its non-pierced end adhering to that end surface of the nebulization chamber comprising the discharge holes for the air laden with the medicament in finely divided form, the capsule having been urged against the holes by the moving air. This adherence of the capsule to the air discharge holes not only impedes capsule movement so preventing release of the medicament, but also prevents the air already laden with medicament from flowing through the discharge holes, which are blocked.

It has also been found that regular and complete emptying of the capsule always occurs when this latter undergoes a precession movement, the vertex of the precession cone being situated in a restricted zone within the top of said spherical cap of the nebulization chamber.

Consequently, the obviate the aforesaid problems, the capsule must continuously undergo the aforesaid precession movement during inhalation, this being sufficient to ensure regular and complete emptying of the capsule.

This object is attained by the inhaler according to the invention, characterized in that the end surface of the nebulization chamber in the zone containing the holes for the discharge of air laden with the finely divided medicament is shaped such that the capsule, when during inhalation it rests on said end surface by its relative spherical cap shaped end, does not impede air passage through any of the discharge holes; the nebulization chamber, at least in that part thereof closest to said discharge holes, tapering towards said end surface of the chamber comprising the discharge holes.

In this manner, as the side wall of the nebulization chamber is no longer entirely cylindrical (by virtue of now comprising a tapered portion), the capsule can no longer undergo rolling while maintaining its axis parallel to the chamber axis. Said particular shape of the chamber surface in the discharge hole zone also prevents the aforesaid adhesion which, as stated, hinders both capsule movement and air discharge.

Consequently the particular structure of the nebulization chamber of the inhaler according to the invention obviates the phenomena which cause irregular and incomplete emptying of the capsule. Thus complete and regular emptying of the capsule is obtained by using the inhaler according to the invention.

In particular, according to one embodiment of the invention, pegs, ribs or like protuberances project into that zone of the end surface of the nebulization chamber in which said discharge holes are provided. These protuberances prevent the capsule blocking one or more discharge holes when resting against said perforated zone of the chamber end surface. In this manner those adherence phenomena which hinder the capsule movement and air discharge are eliminated.

In particular, the surface of said perforated end zone can be conveniently shaped as a spherical cap of size slightly greater than that of the corresponding spherical cap shaped end of the capsule.

In a modified embodiment of the invention, said surface of the perforated end zone of the nebulization chamber is in the form of a grid formed from braided wires. Because of the braided-wire formation of the grid the capsule, even though resting against the grid, is unable to completely obstruct any of the holes of this latter, so that the aforesaid adherence phenomena do not occur. The inhaler according to the invention can be of the rechargeable type usable an indefinite number of times, such as that described in the aforesaid U.S.A. patent. It can also be of the once-only usable or disposable type, which when sold already contains a capsule which was inserted into it on assembly of the various components of the inhaler. This is then thrown away after use.

The invention will be more apparent from the description of one embodiment thereof given hereinafter by way of non-limiting example. The description relates to the inhaler of disposable type shown on the accompanying drawings, in which.

Figure 1:
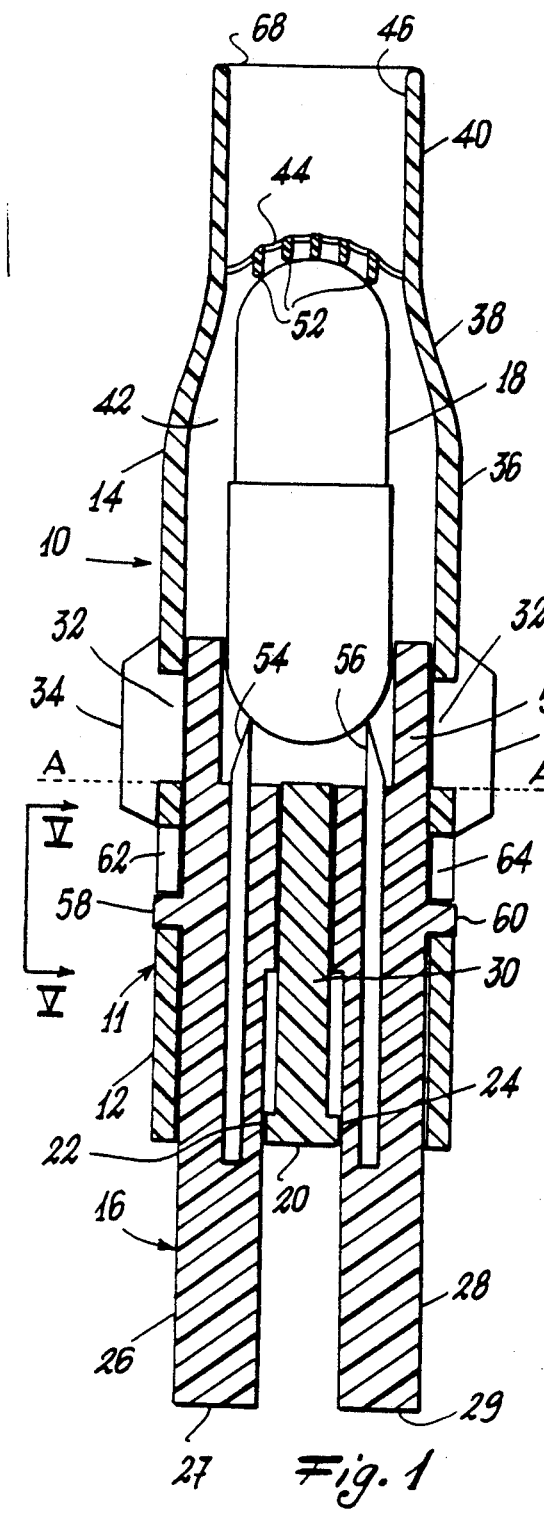
FIG. 1 is an axial longitudinal section on the line I—I of FIG. 3, showing the disposable inhaler of the invention as sold.

The inhaler 10 shown in the figures is of overall cylindrical shape. It is composed substantially of two parts, namely a cylindrical body 11 consisting of a lower part 12 of overall cup shape and an upper part 14 of overall tubular shape, and a piercing device 16 for piercing a capsule 18 of known type containing a medicament in finely divided form. The capsule is visible in FIG. 1 by virtue of having been inserted into the inhaler during its factory assembly.

Figure 3:
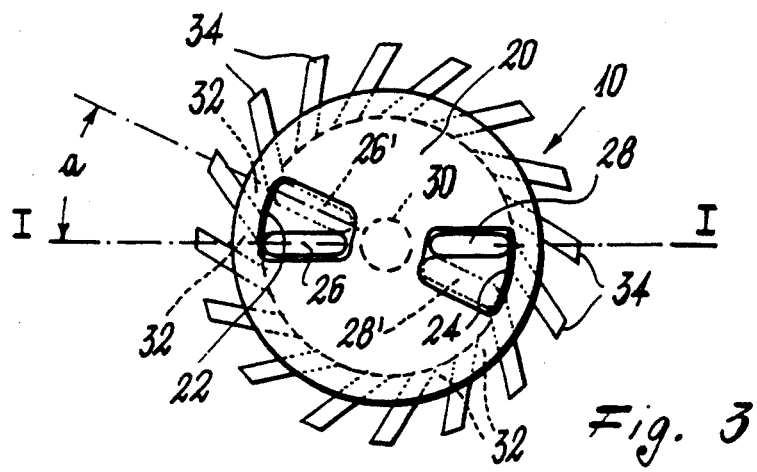
FIG. 3 is a view of the inhaler of FIG. 1 seen from the bottom upwards.

The capsule 18 and piercing device 16 are shown in FIG. 1 in the position which they occupy at the time of sale of the inhaler. As can be seen in FIG. 3, the base wall 20 of the lower part 12 of the inhaler comprises two through apertures 22 and 24 substantially of circular sector shape. Through each of these apertures there projects a shaft 26 and 28 respectively, forming part of the piercing device. The lower part 12 of the cylindrical body 11 comprises in its interior a coaxial cylindrical element 30 which is integral with the base wall 20 and extends upwards to the level AA (FIG. 1) of the upper edge of the lower part 12. The outer side wall of the upper part 14 of the cylindrical body 11 is composed of a cylindrical lower portion 36 which via a substantially frusto-conical portion 38 connects to an upper cylindrical portion 40 of smaller diameter than the lower portion 36.

The lower portion 36 comprises a series of identical rectangular slits 32, the central plane of which does not pass through the longitudinal axis of the cylindrical body 11, but is parallel to this axis such that each slit 32 is at the same distance therefrom. The purpose of this is to generate a swirling air flow on inhalation, as already explained in said U.S.A. patent.

To prevent the fingers inadvertently closing part of the slits 32 on using the inhaler, so reducing the air flow entering through said slits, external fins 34 are provided on the outside of the upper part 14 of the cylindrical body 11 to laterally delimit the slits 32, they having substantially the same orientation as these latter. This arrangement enables the air to enter through all the slits 32 even when the fingers rest in positions corresponding with said slits.

The upper part 14 of the cylindrical body 11 comprises in its interior a coaxial nebulization chamber intended to contain the capsule 18. The chamber 42 is lowerly of cylindrical shape, which tapers upwards in frusto-conical form to finally connect to the cylindrical discharge duct 46. The nebulization chamber 42 is bounded upperly by a perforated partition element 44 which separates it from the discharge duct 46.

Figure 2:
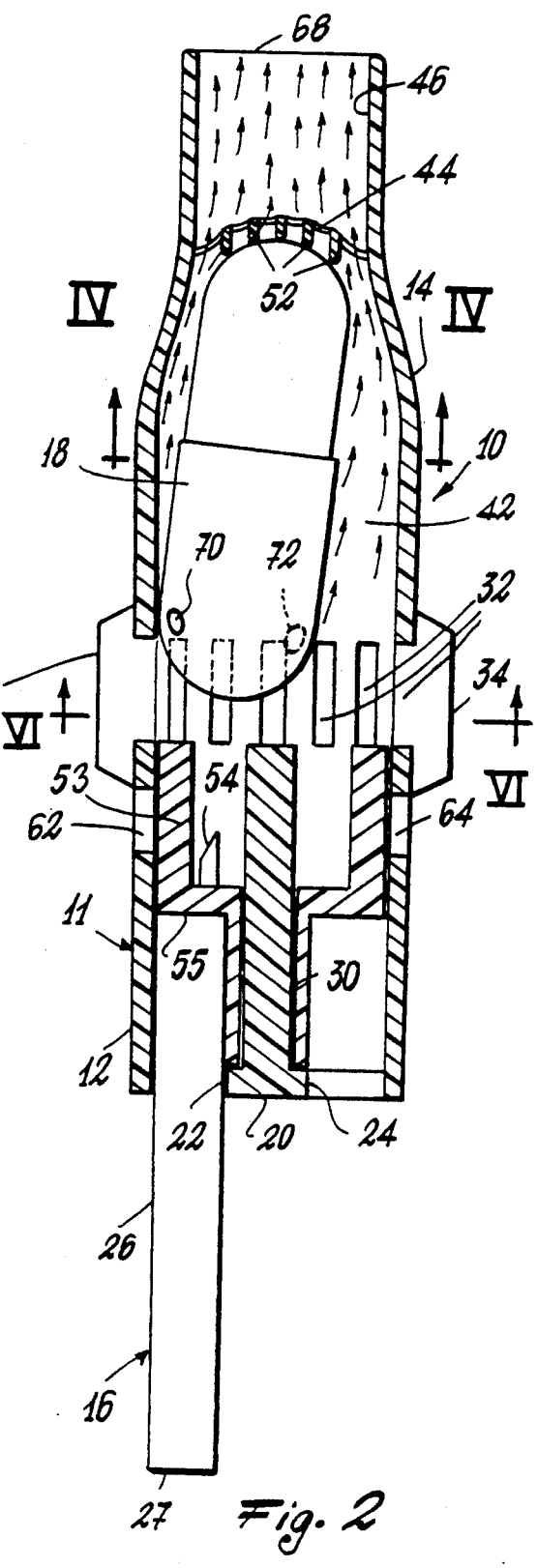
FIG. 2 is a longitudinal section analogous to that of FIG. 1, showing the inhaler ready for inhalation with the capsule already pierced.
Figure 4:
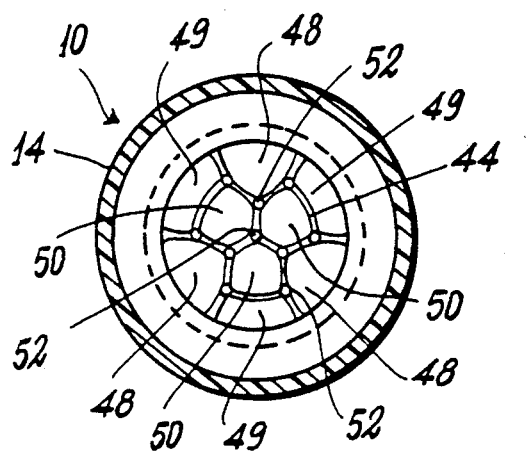
FIG. 4 is a cross-section therethrough on the line IV—IV of FIG. 1, the capsule not being shown for greater clarity.

The partition element is substantially dome shaped and comprises relatively large holes 48, 49 and 50, shown clearly in FIG. 4. A specific characteristic of the partition element 44 is that it comprises pegs 52 projecting inwards parallel to the longitudinal axis of the cylindrical body 11, their purpose being apparent from FIG. 2. As can be seen from this figure, the air flow entering through the slits 32 and represented by arrows can freely pass through all the holes 48, 49 and 50, even when the capsule 18 dragged by the air flow rests with its upper part against the partition element 44.

Consequently adherence of the capsule 18 against the partition element 44 with the blocking of one of its holes cannot take place, as instead can happen with the inhaler of U.S. Pat. No. 4,069,819. Said partition element can obviously be different from that described. It can for example consist of a grid formed from braided wires, thus again preventing blockage of any of the holes in the grid by virtue of the grid shape.

The piercing device 16 comprises a tubular shaped portion 53 having a lower closure wall 55 (FIG. 2) in the form of a circular ring, through the central hole of which there can slide the cylindrical element 30. The piercing device 16 also comprises the two said lower shafts 26 and 28, which extend downwards parallel to the longitudinal axis of the cylindrical body 11. In each of the two shafts 26 and 28 there is embedded a piercing element 54 and 56 respectively, the upper end of which projects in the shape of a flute mouthpiece. The piercing elements 54 and 56 can be metal or hard plastic pointed elements.

Figure 5:
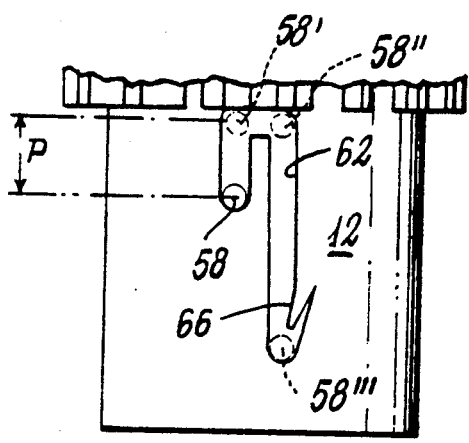
FIG. 5 is a partial side view on the line V—V of FIG. 1, its purpose being to show how the capsule piercing device is guided into and locked in its final position.

The piercing device 16 is provided with a means for guiding it into and locking it in its final position. This guide means consists of a pair of opposing pins 58 and 60, one for each of the two shafts 26 and 28, arranged to slide in respective identical opposing guides 62, 64 of U-shape (see FIG. 5 which shows one of these guides).

As stated, in FIG. 1 the piercing device 16 is shown in the position which it occupies on purchase of the inhaler. The capsule 18 is maintained in a coaxial position because of the presence of the tubular portion 53 of the piercing device 16, which acts as a centerer for the capsule 18. The piercing points 54 and 56 also contribute to keeping the capsule 18 at rest but without piercing it, seeing that at most only the weight of the capsule acts on said points, this certainly being insufficient to produce piercing.

The piercing device 16 is constructed of such dimensions that no clearances or gaps of appreciable size exist between it and the cylindrical body 11 containing it. The reason for this is to ensure that the air entering the nebulization chamber 42 on inhalation has passed practically entirely through the inlet slits 32.

As stated, the capsule 18 is inserted into the nebulization chamber during the assembly of the various parts (12, 14 and 16) forming the inhaler, before the lower part 12, into which the piercing device 16 has been previously inserted, is fixed to the upper part 14, for example by gluing, ultrasonic welding or similar methods.

To use the described disposable inhaler 10, the capsule 18 must firstly be pierced. This is done by pressing against the lower ends 27 and 29 of the shafts 26 and 28 respectively, so that the shafts move inwards through a certain distance equal to the distance p through which the pins 58, 60 move in their grooves 62, 64 in reaching their upper position (see the reference numeral 58' in FIG. 5).

In this manner the points 54 and 56 penetrate the capsule 18, so piercing it.

Figure 6:
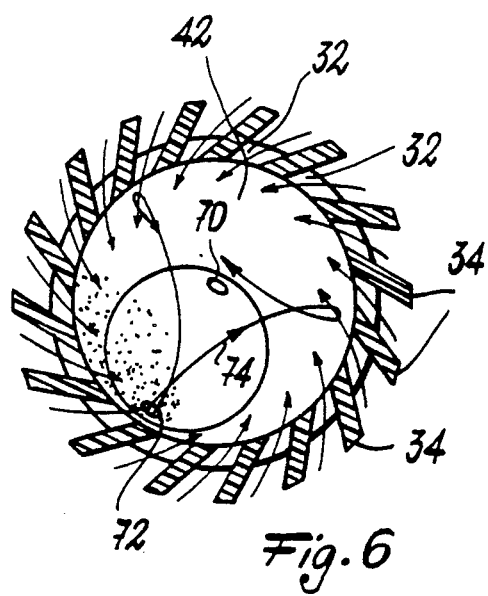
FIG. 6 is a cross-section on the line VI—VI of FIG. 2, showing the trajectory of one of the capsule holes during the precession movement of the capsule, which is seen from below.

A torque must now be applied to the two shafts 26, 28 to turn the entire piercing device 16 about the longitudinal axis of the cylindrical body 11. The relative turning angle is indicated by a (FIG. 3). After this turning operation the two shafts 26, 28 assume the new position 26', 28', with which the new position (58" in FIG. 5) of the pins 58 and 60 corresponds. This causes the capsule 18 to turn through the angle a by being dragged by the points 54 and 56 which are still inserted in it. Finally, the projecting ends of the shafts 26 and 28 are gripped by the fingers and pulled axially outwards until the shafts 26 and 28 are in the position 26', 28' shown by dashed lines in FIG. 3, to which the final position (58''' in FIG. 5) of the pins 58 and 60 corresponds, this being a non-return position because of the presence of the elastic element 66 for locking the pins 58, 60 and hence the entire piercing device 16 in the final position. At this point the inhaler 10 is ready for use, it being necessary only for the user to apply the exit 68 of the discharge duct 46 to his mouth or a nostril and then breath in. Air is sucked through the now open slits 32 to generate a swirl which causes the capsule to undergo the required precession movement, this being the most suitable for completely expelling the finely divided medicament contained in the capsule 18 through the holes 70, 72. It has been found that during the precession movement, each hole 70, 72 describes substantially a hypocycloid trajectory of the type indicated schematically by 74 in FIG. 6, the air entering through the slits 32 being represented by the arrows. The maximum emission of finely divided granules, represented in the figure by dots, takes place during the loop portions of the trajectory 74. By virtue of the upward swirling air flow through the nebulization chamber 42, the finely divided granules expelled from the capsule 18 are entrained upwards, passing by the side of the capsule to emerge with the air through the holes 48, 49, 50 (FIG. 4) of the partition element 44, to then flow through the discharge duct 46 and into the oral or nasal cavity of the user. After this, the inhaler 10 can be thrown away.

Instead of the pins 58 and 60 sliding in their grooves 62 and 64, other methods can obviously be used for guiding the piercing device 16 and locking it in its final position.

A considerable number of tests have shown that in all cases complete emptying of the capsule is obtained, no case in which this has not happened having ever been encountered.

As already stated, instead of the once-only or disposable type, the inhaler according to the invention can be of the multiple use or rechargeable type such as that described in U.S. Pat. No. 4,069,819, the nebulization chamber having however obviously to possess the aforesaid characteristics according to the present invention.

Besides its use in administering common medicaments by inhalation, the inhaler according to the invention has proved particularly useful in administering calcitonin, parathyroid hormone and gonadorelin, each vehicled with mannitol or other suitable vehicles.

We claim:

1. An inhaler for administering medicaments in finely divided form contained in capsules, comprising:
   a body enclosing a nebulization chamber, said nebulization chamber having a circular cross-section and being sufficiently large to enable the capsule to move during inhalation, said nebulization chamber further including:
   (i) a plurality of air discharge apertures disposed at one end of said chamber whereby the air laden with said finely divided medicament may be drawn out of said chamber; and
   (ii) a plurality of air inlet apertures provided near the end of the chamber opposite to said air discharge apertures, said inlet apertures allowing said chamber to communicate with the outside and said air inlet apertures being formed in such a manner as to generate within the chamber during inhalation a swirling air flow which passes through said air discharge apertures; and
   (b) a piercing device which is movable within said body for the purpose of piercing the capsule at one end;
   wherein the end surface of said nebulization chamber near said air discharge apertures is shaped such that when the capsule rests on said end surface during inhalation, said capsule does not substantially prevent air passage through any of the air discharge apertures, said nebulization chamber being tapered towards the end surface of said chamber which includes said air discharge apertures.

2. An inhaler as claimed in claim 1, wherein the end surface of the nebulization chamber which includes the air discharge apertures further comprises pegs, ribs or like protuberances which prevent the capsule, when resting against said end surface, from blocking one or more of said discharge holes.

3. An inhaler as claimed in claim 1, wherein the zone of the end surface of the nebulization chamber containing the air discharge apertures is shaped as a dome with dimensions slightly greater than those of the corresponding spherical cap-shaped end of the capsule.

4. An inhaler as claimed in claim 1, characterised in that that zone of the end surface of the nebulization chamber containing the air discharge apertures is in the form of a grid formed from braided filaments, such as wires or the like.

5. An inhaler as claimed in claim 4 characterized in that the air enters the nebulization chamber through slits spaced angularly equidistant about the longitudinal axis of the nebulization chamber, said slits being disposed in the side wall of the nebulization chamber, said slits being orientated non-radial relative to said axis of the nebulization chamber and the middle plane through each slit being at the same distance from said longitudinal axis.

6. An inhaler as claimed in claim 5, wherein the air inlet slits are delimited laterally by external fins having substantially the same orientation as the slits, said fins extending out from the outer periphery of said body.

7. An inhaler as claimed in claim 1, wherein said body includes resealable means for opening said nebulization chamber whereby spent capsules may be removed and new capsules inserted into said nebulization chamber, whereby said inhaler may be reused multiple times.

* * * * *